(12) United States Patent
Panasci et al.

(10) Patent No.: US 8,492,383 B2
(45) Date of Patent: Jul. 23, 2013

(54) COMBINATION OF A NITROGEN MUSTARD ANALOGUE AND IMATINIB FOR TREATMENT OF CHRONIC LYMPHOCYTIC LEUKEMIA

(75) Inventors: Lawrence C Panasci, Dollard des Ormeaux (CA); Raquel S Aloyz, Montreal (CA)

(73) Assignee: Jewish General Hospital, Montreal, Quebec (CA)

( * ) Notice: Subject to any disclaimer, the term of this patent is extended or adjusted under 35 U.S.C. 154(b) by 513 days.

(21) Appl. No.: 12/543,868

(22) Filed: Aug. 19, 2009

(65) Prior Publication Data

US 2009/0312290 A1    Dec. 17, 2009

Related U.S. Application Data

(63) Continuation of application No. 10/534,573, filed as application No. PCT/IB03/05454 on Nov. 10, 2003, now abandoned.

(60) Provisional application No. 60/425,481, filed on Nov. 12, 2002.

(51) Int. Cl.
*A61K 31/497* (2006.01)
*A61K 31/505* (2006.01)
*A61K 31/196* (2006.01)

(52) U.S. Cl.
USPC ............... 514/252.18; 514/272; 514/567

(58) Field of Classification Search
None
See application file for complete search history.

(56) References Cited

U.S. PATENT DOCUMENTS 5,506,257 A    4/1996    MacLeod et al.

FOREIGN PATENT DOCUMENTS

WO    03 094904    11/2003

OTHER PUBLICATIONS

CLL Trialists' Collaborative Group. Journal of the National Cancer Institute, 1999, vol. 91, No. 10, pp. 861-868.*
Kantarjian et al. N. Engl. J. Med., Feb. 28, 2002, vol. 346, pp. 645-652.*
Vironis et al., "A role for c-Abl tyrosine kinase in p53 upregulation and apoptosis in B-CLL cells exposed to chlorambucil," Blood, vol. 96(11), Part 1, p. 82A (2000).

Ugo et al., "Actualites sur les hemopathies malignes," Bulletin Du Cancer, vol. 89(1), 2002, pp. 75-88 (2002).
De Witte et al., "Highlights and strategies of the EORTC Leukemia Group," European Journal of Cancer, vol. 38, pp. 94-99 (2002).
Soubeyran P., "Oral chemotherapy in hematology," Oncologie 2002 France, vol. 4(6), pp. 373-375 (2002).
Aloyz R. et al., "STI571 sensitized CLL lymphocytes to chlorambucil," Proceedings of the American Association for Cancer Research Annual, vol. 44, pp. 1107 (2003).
Andritsos et al., "Chronic Lymphocytic Leukemia," Current Treatment Options in Oncology, Jun. 2002; vol. 3(3), pp. 225-231 (2002).
Aloyz et al., "Imatinib Sensitizes CLL lymphocytes to chlorambucil," Leukemia, vol. 18, pp. 409-414 (2004).
Esteve Jordi: "Simultaneous occurrence of b-cell chronic lymphocytic leukemia and chronic myeloid leukemia with further evolution to lymphoid blast crisis", Haematologica 1997; vol. 82, pp. 596-599.
Kimby et al: "A systematic overview of chemotherapy effects in b-cell chronic lymphocytic leukaemia", Acta Oncol. 2001, vol. 40, Nos. 2-3, pp. 224-230 (abstract attached).
Tallman M.S.: "Advancing the treatment of hematologic malignancies through the development of targeted interventions", Semin, Hematol, 2002, vol. 39, No. 4, suppl. 3, pp. 1-5 (abstract attached).

\* cited by examiner

*Primary Examiner* — James D Anderson
(74) *Attorney, Agent, or Firm* — Stephen Johnson; George Dohmann

(57) ABSTRACT

The invention relates to a combination which comprises (a) a nitrogen mustard analogue selected from chlorambucil, chlornaphazine, estramustine, mechlorethamine, mechlorethamine oxide hydrochloride, navembichin, phenestrine, prednimustine, trofosfamide or uracil mustard and (b) 4-(4-methylpiperazin-1-ylmethyl)-N-[4-methyl-3-(4-pyridin-3-yl)pyrimidin-2-ylamino)phenyl]-benzamide of formula

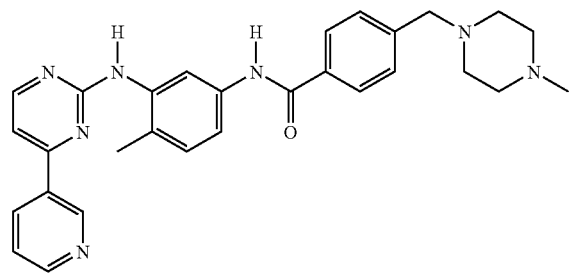

or a pharmaceutically acceptable salt thereof, the invention pertains to the use of said combination for the treatment chronic lymphocytic leukemia.

5 Claims, No Drawings

COMBINATION OF A NITROGEN MUSTARD ANALOGUE AND IMATINIB FOR TREATMENT OF CHRONIC LYMPHOCYTIC LEUKEMIA

This is a continuation of application Ser. No. 10/534,573 filed on Nov. 2, 2005, which is a National Stage of International Application No. PCT/IB03/05454 filed on Nov. 10, 2003, which claims the benefit of U.S. Provisional Application No. 60/425,481 filed Nov. 12, 2002, the entire disclosures of which are hereby incorporated by reference.

The invention relates to a combination which comprises (a) a nitrogen mustard analogue selected from chlorambucil, chlornaphazine, estramustine, mechlorethamine, mechlorethamine oxide hydrochloride, navembichin, phenestrine, prednimustine, trofosfamide or uracil mustard and (b) 4-(4-methylpiperazin-1-ylmethyl)-N-[4-methyl-3-(4-pyridin-3-yl)pyrimidin-2-ylamino)phenyl]-benzamide (hereinafter: "Compound I"); a pharmaceutical composition comprising such a combination and optionally at least one pharmaceutically acceptable carrier for simultaneous, separate or sequential use, in particular for the treatment chronic lymphocytic leukemia (CLL); the use of such a combination for the preparation of a medicament for the treatment of CLL; a commercial package or product comprising such a combination; and to a method of treatment of a warm-blooded animal, especially a human.

Chronic lymphocytic leukemia (CLL) is the most frequent form of leukemia in adults accounting for 25% of all leukemias (approximately 10,000 new CLL cases yearly in the United States (US)). In the US, 95% of CLL cases are B-cell phenotype leukemia. About 50% of CLL, patients are asymptomatic at diagnosis. The stage of disease correlates with prognosis; stage O having a median survival of >10 years while stage I-II has a median survival of 7 years. Treatment is usually started when patients are symptomatic.

There are two major groups of drugs utilized in the treatment of CLL: (1) alkylating agents such as chlorambucil (CLB) or cyclophosphamide and (2) purine analogs such as fludarabine. These agents produce responses in 60-75% of patients.

Recent randomized trials demonstrated a higher response rate for fludarabine as compared to CLB but no difference in survival. Either agent is acceptable as front line therapy in CLL. Other agents are available for therapy. Eventually, all patients become resistant to the drugs. There is no therapy capable of curing this disease (Kalil, N. and Cheson, B. D. The Oncologist 4:352-369, 1999).

The combination partner (b) Compound I is 4-(4-methylpiperazin-1-ylmethyl)-N-[4-methyl-3-(4-pyridin-3-yl)pyrimidin-2-ylamino)phenyl]-benzamide having the following formula

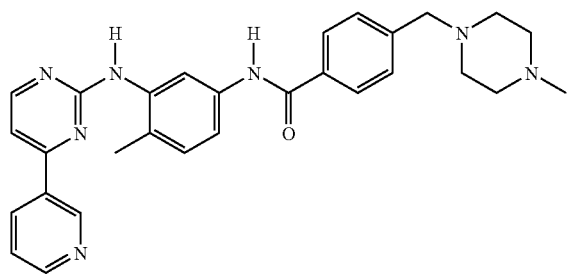 [SMILES: Cc1ccc(NC(=O)c2ccc(CN3CCN(C)CC3)cc2)cc1Nc1nccc(-c2cccnc2)n1]

It can be prepared and administered as described in WO 99/03854, hereby incorporated by reference.

The monomethanesulfonic acid addition salt of Compound I (hereinafter "Salt I") and a preferred crystal form thereof are described in WO 99/03854 published on Jan. 28, 1999.

The structure of the active agents cited may be taken from the actual edition of the standard compendium "The Merck Index" or from databases, e.g. Patents International, e.g. IMS World Publications. The corresponding content thereof is hereby incorporated by reference. Any person skilled in the art is fully enable, based on these references, to manufacture and test the pharmaceutical indications and properties in standard test models, both in vitro and in vivo.

It will be understood that references to the combination partners (a) and (b) are meant to also include their respective pharmaceutically acceptable salts. If the combination partner has at least one basic group, it can form acid addition salts. The combination partner having an acid group, for example COOH, can also form salts with bases. The combination partner (a) or (b) or a pharmaceutically acceptable salt thereof may also be used in form of a hydrate or include other solvents used for crystallization. The 4-(4-methylpiperazin-1-ylmethyl)-N-[4-methyl-3-(4-pyridin-3-yl)pyrimidin-2-ylamino)phenyl]-benzamide, i.e. combination partner (b), is preferably used in the present invention in the form of its monomethanesulfonate salt, e.g. the beta crystal form of the monomethanesulfonate salt.

Compound I is used as a first line treatment of chronic myelogenous leukemia (CML) and Philadelphia chromosome-positive acute lymphoblastic leukemia (ALL). Virtually, all CML cases express a constitutively active c-able kinase as a consequence of the t(9, 22) (q34, 11) translocation. In contrast, in CLL patients, BCR/ABL translocations have not been reported.

Unexpectedly, it has been found that the anti-proliferative effect on cells from patients with chronic lymphocytic leukemia of a combination comprising a nitrogen mustard analogue, especially, chlorambucil and Compound I is greater than the maximum effect that can be achieved with either type of ingredient alone.

The present invention reports that a combination comprising a nitrogen mustard analogue selected from chlorambucil) chlornaphazine, estramustine, mechlorethamine, mechlorethamine oxide hydrochloride, navembichin, phenestrine, prednimustine, trofosfamide or uracil mustard, particularly chlorambucil (CLB) and Compound I, can produce a therapeutic effect which is greater than that obtainable by administration of a therapeutically effective amount of either a sole nitrogen mustard analogue, in particular chlorambucil or the sole Compound I.

The present invention pertains to a combination for simultaneous, separate or sequential use, such as a combined preparation or a pharmaceutical fixed combination, which comprises (a) a nitrogen mustard analogue and (b) Compound I in which the active ingredients (a) and (b) are present in each case in free form or in the form of a pharmaceutically acceptable salt, and optionally at least one pharmaceutically acceptable carrier.

The term "a combined preparation", as used herein defines especially a "kit of parts" in the sense that the combination partners (a) and (b) as defined above can be dosed independently of each other or by use of different fixed combinations with distinguished amounts of the combination partners (a) and (b), i.e. simultaneously or at different time points. The parts of the kit of parts can then, e.g. be administered simultaneously or chronologically staggered, that is at different time points and with equal or different time intervals for any part of the kit of parts. Very preferably, the time intervals are chosen such that the effect on the treated disease in the combined use of the parts is larger than the effect which would be obtained by use of only any one of the combination partners (a) and (b). The ratio of the total amounts of the combination partner (a) to the combination partner (b) to be administered in the combined preparation can be varied, e.g. in order to cope with the needs of a patient sub-population to be treated or the needs of the single patient which different needs can be due to age, sex, body weight, etc. of the patients. Preferably, there is at least one beneficial effect, e.g. a mutual enhancing of the effect of the combination partners (a) and (b), in particular a synergism, e.g. a more than additive effect, additional advantageous effects, less side effects, a combined therapeutic effect in a non-effective dosage of one or both of the combination partners (a) and (b), and very preferably a strong synergism of the combination partners (a) and (b).

The term "treatment" comprises the administration of the combination partners to a warm-blooded animal in need of such treatment with the aim to cure the disease or to have an effect on disease regression or on the delay of progression of a disease.

The term "delay of progression" as used herein means that the disease progression is at least slowed down or hampered by the treatment and that patients exhibit higher survival rates than patients not being treated or being treated with the mono-therapy.

By "nitrogen mustard analogue" is meant chlorambucil, chlornaphazine, estramustine, mechlorethamine, mechlorethamine oxide hydrochloride, navembichin, phenestrine, prednimustine, trofosfamide, uracil mustard.

The term "chlorambucil-resistant chronic lymphocytic leukemia" as used herein defines especially a chronic lymphocytic leukemia in which chlorambucil is no longer efficient or shows a reduction of its therapeutic effectiveness.

Chlorambucil can be prepared according to the process described in U.S. Pat. No. 3,046,301, hereby incorporated by reference.

A combination which comprises (a) a nitrogen mustard analogue, preferably chlorambucil and (b) Compound I in which the active ingredients are present in each case in free form or in the form of a pharmaceutically acceptable salt and optionally at least one pharmaceutically acceptable carrier, will be referred to hereinafter as a COMBINATION OF THE INVENTION.

The COMBINATIONS OF THE INVENTION inhibit chronic lymphocytic leukemia. Furthermore, the COMBINATIONS OF THE INVENTION exhibit beneficial effects in the treatment of chronic lymphocytic leukemia. In one preferred embodiment of the invention, the proliferative disease to be treated with a COMBINATION OF THE INVENTION is chronic lymphocytic leukemia and preferably chlorambucil-resistant chronic lymphocytic leukemia.

All the more surprising is the experimental finding that in vivo on human, the administration of a COMBINATION OF THE INVENTION compared to a monotherapy applying only one of the pharmaceutically active ingredients used in the COMBINATION OF THE INVENTION results not only in a more beneficial, especially synergistic, e.g. anti-proliferative effect, e.g. with regard to the delay of progression of the leukemia disease, but also in further surprising beneficial effects, e.g. less side-effects and a decreased mortality and morbidity. The COMBINATIONS OF THE INVENTION are suitable in particular in the treatment of chronic lymphocytic leukemia refractory to chemotherapeutics known as anti-cancer agents such as chronic lymphocytic leukemia refractory to nitrogen mustard analogue treatment, especially refractory to chlorambucil treatment.

A further benefit is that lower doses of the active ingredients of the COMBINATION OF THE INVENTION can be used, for example, that the dosages need not only often be smaller but are also applied less frequently, or can be used in order to diminish the incidence of side-effects, e.g. diarrhea or nausea, observed with one of the combination partners alone. This is in accordance with the desires and requirements of the patients to be treated.

It can be shown by established test models that a COMBINATION OF THE INVENTION results in the beneficial effects described herein before. The person skilled in the pertinent art is fully enabled to select a relevant test model to prove such beneficial effects. The pharmacological activity of a COMBINATION OF THE INVENTION may, for example, be demonstrated in a clinical study or in a test procedure as essentially described hereinafter.

Suitable clinical studies are in particular randomized, double-blind, parallel studies in cancer patients with late stage disease. Such studies are, in particular, suitable to compare the effects of a mono-therapy using the active ingredients and a therapy using a COMBINATION OF THE INVENTION, and to prove in particular the synergism of the active ingredients of the COMBINATIONS OF THE INVENTION. The primary endpoints in such studies can be the effect on pain scores, analgesic use, performance status, Quality of Life scores or time to progression of the disease. The evaluation of tumors by in regular time periods, e.g. every 4, 6 or 8 weeks, is a suitable approach to determine the effect of the COMBINATION OF THE INVENTION. In a suitable study design, patients are, for example, receiving per treatment cycle of 2 weeks, Compound I daily at a dose ranging from 50 to 1000 mg of the active substance and chlorambucil at a dose ranging from 0.2 to 1 mg/kg/day. The minimum duration of such a study should be about, e.g. 4 weeks.

It is one objective of this invention to provide a pharmaceutical composition comprising a quantity, which is jointly therapeutically effective against chronic lymphocytic leukemia comprising the COMBINATION OF THE INVENTION. In this composition, the combination partners (a) and (b) can be administered together, one after the other or separately in one combined unit dosage form or in two separate unit dosage forms. The unit dosage form may also be a fixed combination.

The pharmaceutical compositions according to the invention can be prepared in a manner known per se and are those suitable for enteral, such as oral or rectal, and parenteral administration to mammals (warm-blooded animals), including man, comprising a therapeutically effective amount of at least one pharmacologically active combination partner alone or in combination with one or more pharmaceutically acceptable carries, especially suitable for enteral or parenteral application. In one embodiment of the invention, one or more of the active ingredients are administered orally.

The novel pharmaceutical composition contain, for example, from about 10% to about 100%, preferably from about 20% to about 60%, of the active ingredients. Pharmaceutical preparations for the combination therapy for enteral or parenteral administration are, for example, those in unit dosage forms, such as sugar-coated tablets, tablets, capsules or suppositories, and furthermore ampoules. If not indicated otherwise, these are prepared in a manner known per se, for example by means of conventional mixing, granulating, sugar-coating, dissolving or lyophilizing processes. It will be appreciated that the unit content of a combination partner contained in an individual dose of each dosage form need not in itself constitute an effective amount since the necessary effective amount can be reached by administration of a plurality of dosage units.

In particular, a therapeutically effective amount of each of the combination partners of the COMBINATION OF THE INVENTION may be administered simultaneously or sequentially and in any order, and the components may be administered separately or as a fixed combination. For example, the method of delay of progression or treatment of a proliferative disease according to the invention may comprise (i) administration of the first combination partner in free or pharmaceutically acceptable salt form and (ii) administration of the second combination partner in free or pharmaceutically acceptable salt form, simultaneously or sequentially in any order, in jointly therapeutically effective amounts, preferably in synergistically effective amounts, e.g. in daily dosages corresponding to the amounts described herein. The individual combination partners of the COMBINATION OF THE INVENTION can be administered separately at different times during the course of therapy or concurrently in divided or single combination forms. Furthermore, the term administering also encompasses the use of a pro-drug of a combination partner that convert in vivo to the combination partner as such. The instant invention is therefore to be understood as embracing all such regimes of simultaneous or alternating treatment and the term "administering" is to be interpreted accordingly.

The effective dosage of each of the combination partners employed in the COMBINATION OF THE INVENTION may vary depending on the particular compound or pharmaceutical composition employed, the mode of administration, the condition being treated, the severity of the condition being treated. Thus, the dosage regimen the COMBINATION OF THE INVENTION is selected in accordance with a variety of factors including the route of administration and the renal and hepatic function of the patient. A physician, clinician or veterinarian of ordinary skill can readily determine and prescribe the effective amount of the single active ingredients required to prevent, counter or arrest the progress of the condition. Optimal precision in achieving concentration of the active ingredients within the range that yields efficacy without toxicity requires a regimen based on the kinetics of the active ingredients' availability to target sites. This involves a consideration of the distribution, equilibrium, and elimination of the active ingredients.

Chlorambucil, herein after also designated CLB, can be administered at a dose range of 0.1 to 1 mg/kg/day, preferably at a dose range of 0.2 to 0.8 mg/kg/day, most preferably, CLB can be administered at a preferred dose of 0.3 to 0.6 mg/kg/day, e.g. 0.3 mg/kg/day. Chlorambucil can be administered orally. Chlorambucil can be administered, e.g. for 5 consecutive days every four weeks, e.g. at a dose of 0.3 mg/kg of body weight.

In the combination of the invention, Compound I, e.g. Salt 1, can be administered for one day prior to CLB and for 5 days after completing CLB. In one embodiment of the invention, CLB can be administered continuously and Compound I, e.g. Salt 1, can be administered daily. In a further embodiment of the combination of the invention, Compound I and CLB are administered orally daily. In one embodiment of the invention, CLB and Compound I is administered at a daily dose of 400 to 800 mg per day and CLB is administered daily at a dose of 0.1 mg/kg of body weight per day.

In an other aspect of the invention, Compound I, e.g. Salt I, and CLB are administered as a fixed combination.

A further embodiment of the invention pertains to a fixed combination CLB and Compound I, e.g. Salt I.

119.5 mg of Salt I correspond to 100 mg of Compound I (free base) as active substance. Depending on species, age, individual condition, mode of administration, and the clinical picture in question, effective doses of Salt I, for example daily doses corresponding to about 50 to 1000 mg of Compound I, preferably 50 to 600 mg, are administered to warm-blooded animals of about 70 kg bodyweight. For adult patients with chronic lymphocytic leukemia, a starting dose of 400 mg daily can be recommended. For patients with an inadequate response after an assessment of response to therapy with 400 mg daily, dose escalation can be safely considered and patients may be treated as long as they benefit from treatment and in the absence of limiting toxicities.

The invention relates also to a method for administering to a human subject suffering from chronic lymphocytic leukemia, Compound I or a pharmaceutically acceptable salt thereof, which comprises administering daily a pharmaceutically effective amount of Compound I or a pharmaceutically acceptable salt thereof to said human subject for a period exceeding 3 months. The invention relates especially to such method wherein a daily dose of 50 to 800 mg of Compound I, preferably 50 to 400 mg, is administered.

When the combination partners employed in the COMBINATION OF THE INVENTION are applied in the form as marketed as single drugs, their dosage and mode of administration can take place in accordance with the information provided on the packet leaflet of the respective marketed drug in order to result in the beneficial effect described herein, if not mentioned herein otherwise.

The COMBINATION OF THE INVENTION can be a combined preparation or a pharmaceutical composition.

Moreover, the present invention relates to a method of treating a warm-blooded animal having a chronic lymphocytic leukemia comprising administering to said animal a COMBINATION OF THE INVENTION in a quantity which is jointly therapeutically effective against said leukemia and in which the combination partners can also be present in the form of their pharmaceutically acceptable salts. In one embodiment of the invention, in such method the COMBINATION OF THE INVENTION is co-administered with an anti-diarrheal agent. Furthermore, the treatment can comprise radiotherapy, cryotherapy and immunotherapy.

Furthermore, the present invention pertains to the use of a COMBINATION OF THE INVENTION for the treatment of chronic lymphocytic leukemia and for the preparation of a medicament for the treatment of chronic lymphocytic leukemia.

Additionally, the present invention pertains to the use of chlorambucil in combination with Compound I or a pharmaceutically acceptable salt thereof, e.g. Salt 1, for the preparation of a medicament for the treatment of chronic lymphocytic leukemia.

The present invention also pertains to the use of Compound I or a pharmaceutically acceptable salt therefore, e.g. Salt I, in combination with chlorambucil for the preparation of medicament for the treatment of chronic lymphocytic leukemia resistant to chlorambucil.

Moreover, the present invention provides a commercial package comprising as active ingredients COMBINATION OF THE INVENTION, together with instructions for simultaneous, separate or sequential use thereof in the treatment of chronic lymphocytic leukemia.

EXAMPLE 1

Compound I Sensitizes CLL Lymphocytes to CLB

A—Material and Methods

A-1) Isolation of CLL Lymphocytes and cell culture Lymphocytes are isolated from the peripheral blood of CLL patients by sedimentation centrifugation on Ficoll Hypaque (Pharmacia, Uppsala, Sweden) as described previously, e.g. in Christodoulopolis G. et al., Cancer Research, 1999, 5:2178-84. Aliquots containing 1×10$^6$ cells/ml are sent for T-lymphocyte analysis. The percentage of contaminating T lymphocytes is determined using fluorescence-activated cell sorting analysis with CD3 antibody. The percentage of T-lymphocyte contamination in the isolated B-lymphocytes population determined by FACS analysis and expressed as a mean %±SE is 6.4±1.8.

The WSU cell line is a B-lymphocytic cell line derived from a CLL patient (Mohammad R. M., et al., Leukemia, 1996, 10:130-7). The I83 cell line is a B-type chronic lymphocytic leukemia cell line (Carlsson M. et al., Eur. J. Immunol., 1989, 19:913-21).

A-2) Plating Efficiency and Dosing. The lymphocytes and WSU and I83 CLL lymphocytes are seeded into 96-well plates in 200 µl suspensions containing 1.5×10$^6$ lymphocytes/ml and 1.25×10$^5$ cells/ml respectively in RPMI supplemented with 10% FBS. Only dose responses with linear plating efficiencies are analyzed. The lymphocytes are then incubated at 37° C. in the presence of various concentrations of Compound I (0-100 µM) alone, CLB (0-100 µM) alone, or various concentrations of both drugs together.

A-3) Cytotoxic Assay. The MTT assay is performed 72 hours after plating as described before (Christodoulopolis G et al., Cancer Research, 1998, 58:1789-92) by addition of 20 µl of a solution of 5 mg/ml MTT (3-[4,5-dimethylthiazol-2-yl]2,5-diphenyl-tetrazolium bromide) in RPMI media to each well. The LD$_{50}$ of CLB alone, Compound I alone or CLB in the presence of Compound I is defined as to be the drug concentration required to reduce the absorbance reading to 50% of the control value. The percentage of surviving cells after treatment respect to vehicle treated cells (control) is calculated as (OD treated cells/OD untreated cells)×100. Synergy is determined by the formula: a/A+b/B=1 where a is the concentration of CLB required to produce 50% of control values in combination with Compound I at concentration b; A is the concentration of CLB that produces an LD$_{50}$ without Compound I; and B is the concentration of Compound I that produces an LD$_{50}$ in the absence of CLB. According to the formula, when I<1 the interaction is synergistic, when I=1, the interaction is additive, and when I>1 there is an antagonistic interaction.

A-4) Statistical Analysis Differences between mean values is assessed by two tailed t-test. Correlation and linear regression analysis are performed using the EXCEL Statistical Tool Package.

B—Results

B-1) Compound I sensitizes CLL-WSU cell line to chlorambucil The LD$_{50}$ is obtained by exponential interpolation. The CLB LD$_{50}$ alone or in combination with Compound I (5.0 µM or 10 µM) and Compound I LD$_{50}$ alone are determined as described above. The results are expressed as the mean value of three independent experiments±SE (standard error of the mean). The * indicates a significant difference (p<0.005) between the CLB LD$_{50}$ alone versus CLB LD$_{50}$ in the presence of Compound I. The resulting I value (I<), calculated as described above indicates that CLB and Compound I act synergistically.

|  | LD$_{50}$ in µM | I |
|---|---|---|
| CLB alone | 34.00 ± 2.82 | |
| Compound I alone | 13.72 ± 2.75 | |
| CLB + 5 µM Compound I | 5.95 ± 0.17* | 0.53 |
| CLB + 10 µM Compound I | 3.15 ± 1.82* | 0.82 |

Experiments performed with the WSU cell line show that Compound I sensitized these cells to CLB cytotoxicity 10 times. Incubations with CLB alone required a 34 µM dose to produce an LD$_{50}$ while 13.72 µM Compound I alone produced an LD$_{50}$. However, incubations with both drugs simultaneously, resulted in an LD$_{50}$ of 5.95 µM for CLB in the presence of 5.0 µM Compound I (I=0.53) and 3.15 µM in the presence of 10 µM Compound I (I=0.82).

B-2) Compound I Sensitizes CLL-Lymphocytes to Chlorambucil In Vitro

To further assess the effect of Compound I in CLB cytotoxicity, similar in vitro studies are performed using lymphocytes from CLL patients. The patients are categorized as follows in table 1; 7 patients are untreated (U[1]-U[7]) and 5 patients had been previously treated with CLB (T[1]-T[5]).

| | LD$_{50}$ in µM | | | |
|---|---|---|---|---|
| | CLB | Compound I | CLB + Compound I | I |
| U[1] | 14.6 | 55.93 | 3.35 (5 µM Compound I) | 0.318 |
| U[2] | 28.49 | 29.79 | 2.96 (5 µM Compound I) | 0.267 |
| U[3] | 20.02 | 36.8 | 4.7 (5 µM Compound I) | 0.37 |
| U[4] | 54.2 | 101.8 | 21.20 (5 µM Compound I) | 0.587 |
| U[5] | 12.27 | 44.9 | 70.10 (10 µM Compound I) | 5.93 |
| U[6] | 18.08 | 47.9 | 9.80 (20 µM Compound I) | 1.5 |
| U[7] | 7.84 | 46.7 | 3.04 (5 µM Compound I) | 0.496 |
| T[1] | 9.29 | 33.29 | 1.09 (10 µM Compound I) | 0.412 |
| T[2] | 23.1 | 16.5 | 1.10 (10 µM Compound I) | 0.65 |
| T[3] | 5.56 | 53.06 | 2.67 (10 µM Compound I) | 0.66 |
| T[4] | 79.7 | 32.2 | 35.20 (10 µM Compound I) | 0.75 |
| T[5] | 49.2 | 34 | 17.2 (5 µM Compound I) | 0.497 |

The results indicate that both drugs act synergistically in 10 out of 12 patients; out of the 7 untreated patients, 5 showed synergistic effects with Compound I (U[1]-U[4], U[7]); patients U[5] and U[6] with I>1 showed antagonistic results (I=5.93 and I=1.5 respectively). All 5 of the patients who had been previously treated with CLB (T[1]-T[5]) showed synergistic effects. The CLB LD$_{50}$ alone ranged from 5.56 µM to 79.7 µM. The Compound I LD$_{50}$ alone ranged from 16.5 µM to 101.8 µM. Compound I at 2.5-10 µM range decreases the concentration of CLB necessary to produce an LD$_{50}$ to 1.1 µM-35.5 µM.

There is no significant difference between the Compound I LD$_{50}$ of untreated versus treated patients (U[7]-U[4] and U[7] versus T[1]-T[5]) indicating that Compound I sensitizes CLL-lymphocytes to CLB regardless of the clinical status.

These results suggest that Compound I may prove to be beneficial in a clinical setting since synergy is seen at concentrations (<10 µM) attainable in patients with minimal toxicity (Mauro M. J. and Drucker B. J. The Oncologist 2001, 6:233-238). The fact that the sensitization obtained using 5 and 10 µM Compound I is similar, indicates that synergy between both drugs appears not to be dose dependent. This may be due to maximal inhibition of c-abl kinase at <5 µM in patient samples. Compound I pharmacokinetics demonstrates that after oral administration to patients, the Cmax (maximum concentration) occurs at 1-3 hours after administration. The Cmax after a 400 mg dose is 2.35±1.0 µg/ml (≈4.0 µM) and after a 600 mg does is 7.83±3.8 µg/ml (≈13.0 µM). The half life is approximately 12 hours. The concentration, e.g. 10 µM, of Compound I utilized in the above mentioned experiments are clinically obtainable.

EXAMPLE 2

Capsules with 4-[(4-methyl-1-piperazin-1-ylmethyl)-N-[4-methyl-3-[[4-(3-pyridinyl)-2-pyrimidinyl]amino]phenyl]benzamide methanesulfonate, beta crystal form Capsules containing 119.5 mg of Salt I corresponding to 100 mg of Compound I (free base) as active moiety are prepared in the following composition:

| Composition: | | |
|---|---|---|
| | Salt I | 119.5 mg |
| | Cellulose MK GR | 92 mg |
| | Crospovidone XL | 15 mg |
| | Aerosil 200 | 2 mg |
| | Magnesium stearate | 1.5 mg |
| | | 230 mg |

The capsules are prepared by mixing the components and filling the mixture into hard gelatin capsules, size 1.

EXAMPLE 3

Capsules with 4-[(4-methyl-1-piperazin-1-ylmethyl)-N-[4-methyl-3-[[4-(3-pyridinyl)-2-pyrimidinyl]amino]phenyl]benzamide methanesulfonate, beta crystal form Capsules containing 119.5 mg of Salt I corresponding to 100 mg of Compound I (free base) as active moiety are prepared in the following composition:

| Composition: | | |
|---|---|---|
| | Salt I | 119.5 mg |
| | Avicel | 200 mg |
| | PVPPXL | 15 mg |
| | Aerosil | 2 mg |
| | Magnesium stearate | 1.5 mg |
| | | 338.0 mg |

The capsules are prepared by mixing the components and filling the mixture into hard gelatin capsules, size 1.

EXAMPLE 5

The material and methods of example 5 are provided in example 1

B—Results

B-1) Compound I Sensitizes I-83 Cell Line to Chlorambucil

The CLB $IC_{50}$ alone or in combination with Compound I (1.5 μM or 3 μM) and Compound I $IC_{50}$ alone are determined as described above.

| | $LD_{50}$ in μM | I |
|---|---|---|
| CLB alone | 40.66 ± 2.80 | |
| Compound I alone | 33.73 ± 4.19 | |
| CLB + 1.5 μM Compound I | 17.30 ± 1.00* | 0.45 |
| CLB + 3 μM Compound I | 25.40 ± 1.53* | 0.74 |

The * indicates a significant difference (p < 0.005) between the CLB $IC_{50}$ alone versus CLB $IC_{50}$ in the presence of Compound I.

Experiments performed with the I83 cell line using the MTT assay show that Compound I, e.g. Salt I, synergistically sensitized these cells to CLB cytotoxicity 2 fold. Incubation of I83 cells with CLB alone requires a concentration of 40.66 μM to produce an $IC_{50}$ while 33.73 μM of Compound I alone produce an $IC_{50}$. However incubation with both drugs simultaneously, resulted in an $IC_{50}$ of 17.3 μM for CLB in the presence of 1.5 μM of Compound I (I=0.45) and 24.5 μM in the presence of 3.0 μM Compound I (I=0.74).

B-2) Compound I Sensitizes CLL-Lymphocytes to Chlorambucil In Vitro

| | $LD_{50}$ in μM | | | |
|---|---|---|---|---|
| | CLB | Compound I | CLB + Compound I | I |
| $U^1$ | 14.6 | 55.93 | 3.35 (10 μM Compound I) | 0.32 |
| $U^2$ | 28.49 | 29.79 | 2.96 (10 μM Compound I) | 0.27 |
| $U^3$ | 20.02 | 36.8 | 4.7 (5 μM Compound I) | 0.37 |
| $U^4$ | 54.2 | 101.8 | 21.20 (5 μM Compound I) | 0.59 |
| $U^5$ | 12.27 | 44.9 | 79.9 (5 μM Compound I) | 6.5 |
| $U^6$ | 18.08 | 47.9 | 11.70 (5 μM Compound I) | 0.75 |
| $U^6$ | 18.08 | 47.9 | 13.8 (10 μM Compound I) | 0.96 |
| $T^1$ | 9.29 | 33.29 | 1.2 (5 μM Compound I) | 0.28 |
| $T^2$ | 23.1 | 16.5 | 3.0 (5 μM Compound I) | 0.42 |
| $T^3$ | 5.56 | 53.06 | 3.54 (5 μM Compound I) | 0.72 |
| $T^4$ | 79.7 | 32.2 | 59.0 (5 μM Compound I) | 0.88 |

Compound I decreases the concentration of CLB necessary to produce an $IC_{50}$ to 1.1 μM-59 μM.

The invention claimed is:

1. A pharmaceutical combination for simultaneous, separate or sequential use for the treatment of patients with chronic lymphocytic leukemia which comprises (a) chlorambucil- and (b) 4-(4-methylpiperazin-1-ylmethyl)-N-[4-methyl-3-(4-pyridin-3-yl)pyrimidin-2-ylamino)phenyl]-benzamide having the following formula

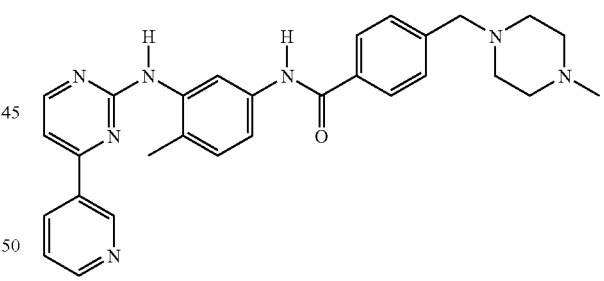

in which the active ingredients (a) and (b) are each present in free form or in the form of a pharmaceutically acceptable salt and wherein (a) chlorambucil is in a dose amount of 0.2 to 0.8 mg/kg of body weight/day and (b) 4-(4-methylpiperazin-1-ylmethyl)-N-[4-methyl-3-(4-pyridin-3-yl)pyrimidin-2-ylamino)phenyl]-benzamide is in a dose amount of 50 mg to 800 mg per day.

2. A method of treating a human patient having chronic lymphocytic leukemia comprising administering simultaneously, separately or sequentially to the human patient in need thereof a pharmaceutical combination comprising: (a) chlorambucil- and (b) 4-(4-methylpiperazin-1-ylmethyl)-N-[4-methyl-3-(4-pyridin-3-yl)pyrimidin-2-ylamino)phenyl]-benzamide having the following formula

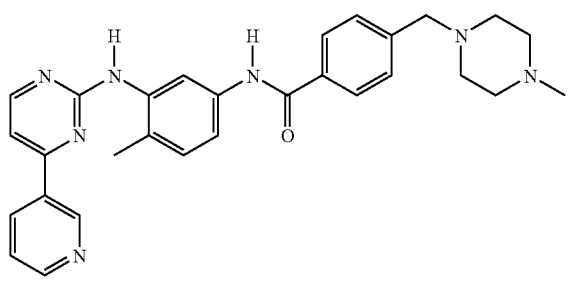 [SMILES: Cc1ccc(NC(=O)c2ccc(CN3CCN(C)CC3)cc2)cc1Nc1nccc(-c2cccnc2)n1]

in which the active ingredients (a) and (b) are each present in free form or in the form of a pharmaceutically acceptable salt and wherein (a) chlorambucil is administered at a dose of 0.2 to 0.8 mg/kg of body weight/day and (b) 4-(4-methylpiperazin-1-ylmethyl)-N-[4-methyl-3-(4-pyridin-3-yl)pyrimidin-2-ylamino)phenyl]-benzamide is administered at a dose of 50 mg to 800 mg per day.

3. A pharmaceutical composition comprising a quantity, which is jointly therapeutically effective against chronic lymphocytic leukemia of the combination according to claim 1 and at least one pharmaceutically acceptable carrier.

4. A commercial package comprising a pharmaceutical composition according to claim 3 together with instructions for simultaneous, separate or sequential use thereof in the treatment of chronic lymphocytic leukemia.

5. A method of treating a human patient having chronic lymphocytic leukemia comprising the step of administering a therapeutically amount of 4-(4-methylpiperazin-1-ylmethyl)-N-[4-methyl-3-(4-pyridin-3-yl)pyrimidin-2-ylamino)phenyl]-benzamide in free form or in the form of a pharmaceutically acceptable salt in combination with chlorambucil.

* * * * *